United States Patent [19]
Outsuka et al.

[11] 4,083,754
[45] Apr. 11, 1978

[54] VOLTAMMETRIC APPARATUS AND METHOD

[75] Inventors: Koremitsu Outsuka, Fukuoka; Kazuyoshi Kawasaki; Yutaka Tanaka, both of Kitakyushu, all of Japan

[73] Assignee: Mitsubishi Kasei Kobyo Kabushiki Kaisha, Tokyo, Japan

[21] Appl. No.: 679,972

[22] Filed: Apr. 26, 1976

[30] Foreign Application Priority Data
Apr. 28, 1975 Japan .................................. 50-51668

[51] Int. Cl.$^2$ ............................................ G01N 27/46
[52] U.S. Cl. ................................ 204/1 T; 204/195 H
[58] Field of Search ................ 204/1 T, 195 R, 195 H

[56] References Cited
PUBLICATIONS
Flato, "Analytical Chemistry", vol. 44, Sep. 1972, pp. 75A–87A.
Florence, et al., "J. of Electroanalytical Chemistry and Interfacial Electrochemistry", vol. 56, No. 2, pp. 301–309, 1974.
Christian, "J. of Electroanalytical Chemistry and Interfacial Electrochemistry" vol. 23, No. 1, 1969, pp. 1–7.

*Primary Examiner*—T. Tung
*Attorney, Agent, or Firm*—Oblon, Fisher, Spivak, McClelland & Maier

[57] ABSTRACT

In apparatus for use in differential pulse anodic stripping voltammetry the period of the pulse voltage is selected to be in a range of from 16.7 to 400 milliseconds for the purpose of analyzing an extremely small quantity of metal ions at high speeds and at high sensitivities.

12 Claims, 20 Drawing Figures

VOLTAMMETRIC APPARATUS AND METHOD

BACKGROUND OF THE INVENTION

This invention relates to voltammetric apparatus, more particularly improved apparatus for use in differential pulse anodic stripping voltammetry (hereinafter abbreviated as DPASV).

DPASV is recognized in the art as an effective method for analyzing a minute quantity of components, especially metals contained in solutions.

Figure 1:
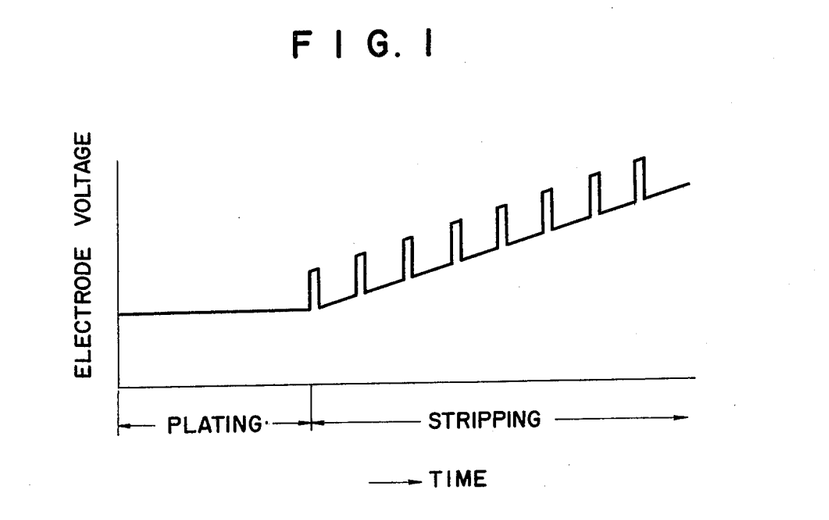
FIG. 1 is a diagram showing one example of the method of applying voltages in DPASV.

The method of DPASV consists essentially of the following two steps. In the first step a plating voltage about several hundreds millivolts negative with reference to the oxidation reduction potential of the component to be analyzed is impressed upon a working electrode immersed in a solution to be measured for plating the working electrode. In the second step a voltage comprising direct current voltage (stripping voltage) which increases gradually with time in the positive direction from the plating voltage and superimposed upon a pulse voltage is applied by sweeping upon the working electrode for stripping the component that has been plated on the working electrode during the first step. For this reason, the second step is termed the stripping step. FIG. 1 of the accompanying drawing is a graph showing the manner of applying the voltage in the first and second steps. Although in FIG. 1 the pulse voltage is shown as being superimposed upon the stripping voltage (sweep potential) on the positive side thereof, it is also possible to superimpose the pulse voltage on the negative side of the stripping voltage.

Figure 2:
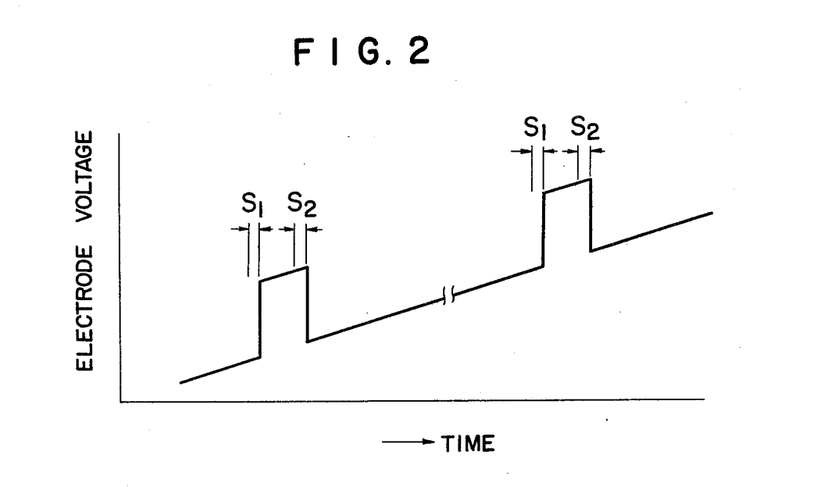
FIG. 2 is a diagram showing the relationship between a pulse and sampling time.

In sweeping during the second step, among the current flowing through the working electrode, the current that flows while the pulse is not applied, preferably the current that flows during a definite interval (sampling time $S_1$) immediately prior to the application of the pulse voltage, and the current that flows while the pulse is applied, preferably a definite interval of the latter half of the pulse (sampling time $S_2$) are measured to obtain sampling currents $IS_1$ and $IS_2$ respectively and the difference between these sampling currents is determined. FIG. 2 diagrammatically shows one example of the relationship between the pulse and the sampling times $S_1$ and $S_2$.

To calculate the difference between sampling currents $IS_1$ and $IS_2$, these currents are usually converted into corresponding sampling voltages which are held by respective voltage holders and then the difference between these sampling voltages is determined. The maximum value or the integrated value of the voltage difference is used to calculate the concentration of the component to be analyzed.

The outline and present state of DPASV can be found in the following papers.

a. J. B. Flato, Analytical Chemistry, Vol. 44, September 1972, pages 75A–87A.
b. H. Siegerman et al., American Laboratory, Vol. 4, No. 6, pages 59 – 68 (1972)
c. T. R. Copeland et al., Analytical Chemistry, Vol. 46, No. 14, Dec. 1974, pages 1257A - 1264A.

One example of the apparatus for use in DPASV is described in U.S. Pat. No. 3,420,764.

Although DPASV is an analytical method having an extremely high sensitivity, it is desirable to improve further the sensitivity.

Figure 3:
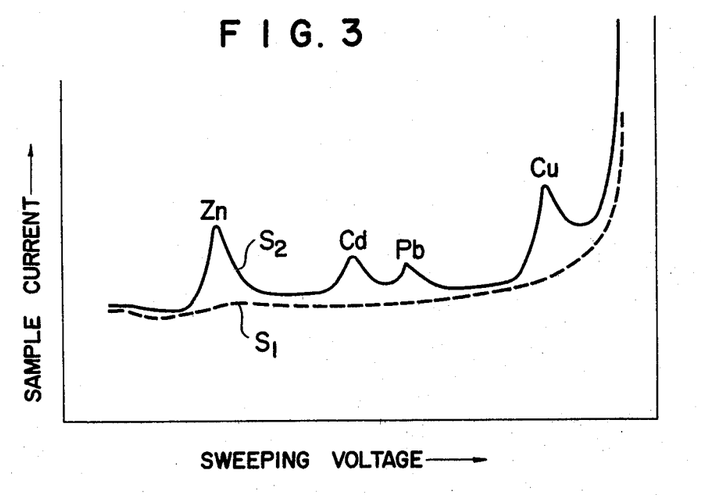
FIG. 3 show one example of curves showing the relationship between sample current and sweep voltage where the pulse period is long.
Figure 4:
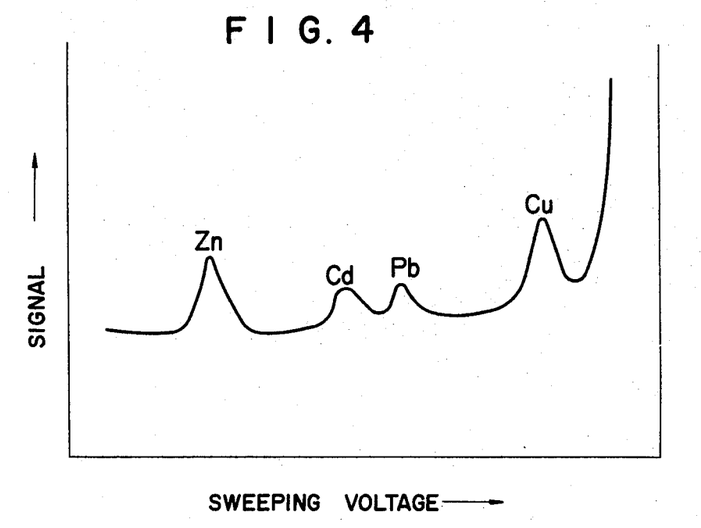
FIG. 4 is a graph showing the relationship between output signal and the sweep voltage in the same case as that shown in FIG. 3.
Figure 5:
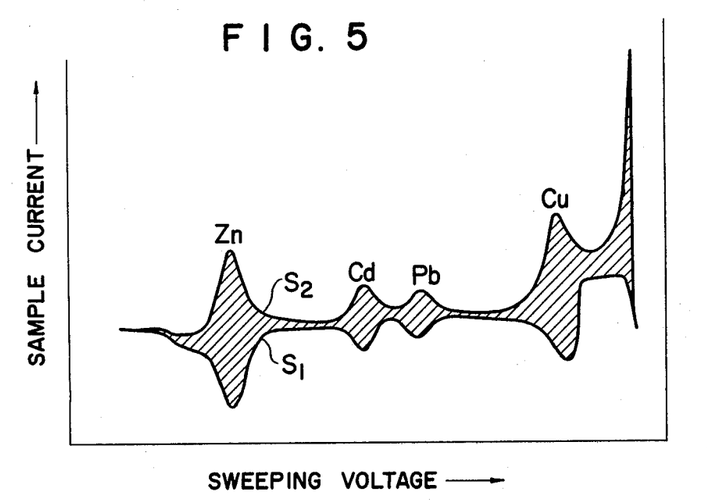
FIG. 5 are graphs showing sample currents obtainable by the apparatus of this invention.
Figure 6:
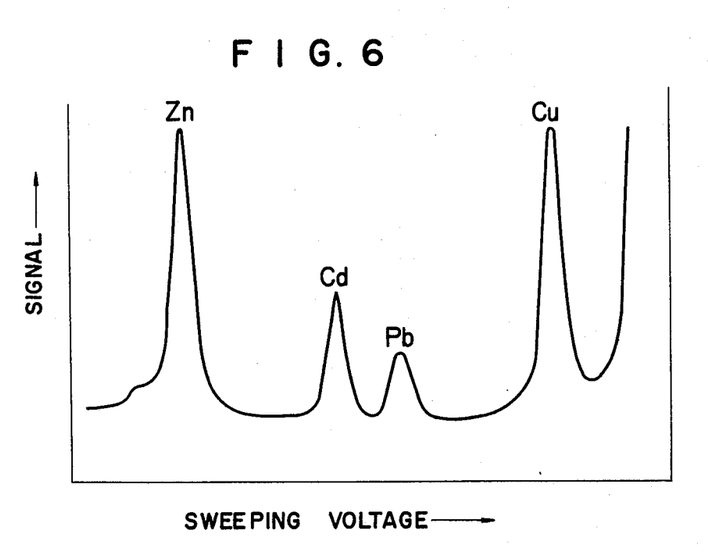
FIG. 6 is a graph showing the output signal in the same case as that shown in FIG. 5.

As a result of an exhaustive investigation regarding the method of voltage sweeping of the working electrode we have found that the current flowing through the working electrode varies in a different manner according to the period (repetition period) of the pulse voltage. More particularly, where the pulse period is long, for example from 0.5 to 5 seconds, the sample current IS does not contain any peak as shown in FIG. 3 whereas sample current $IS_2$ contains peaks corresponding to the components to be analyzed. As has been pointed out before where the pulse voltage is superimposed upon the stripping voltage on the negative side thereof, curve $S_2$ will be positioned beneath curve $S_1$ with its direction inverted. In the case shown in FIG. 3, the difference between $IS_2$ and $IS_1$, is the output signal and is shown by FIG. 4.

Where the period of the pulse is extremely short, for example 116.9 milliseconds, as shown in FIG. 5 although the peaks of sample current $IS_2$ do not change sample current $IS_1$ contains peaks of the opposite polarity and somewhat lag with respect to the peaks of the sample current $IS_2$. Where the pulse voltage is superimposed on the negative side of the stripping voltage the polarities of curves $S_1$ and $S_2$ are reversed and curve $S_2$ is positioned beneath curve S. In any case, the difference between sample currents $IS_2$ and $IS_1$, is the output signal and is shown by FIG. 6.

In this manner, the output signal increases as the pulse period decreases and the sensitivity is improved in proportion thereto.

SUMMARY OF THE INVENTION

It is an object of this invention to provide improved apparatus for use in DPASV having high sensitivities.

Another object of this invention is to provide novel apparatus capable of analyzing a minute quantity of components contained in a solution at high sensitivities and in a short time.

According to this invention, these and further objects can be accomplished by providing apparatus for use in differential pulse anodic stripping voltammetry of the class comprising an electrolytic cell provided with a working electrode and a counter electrode; a source of plating voltage, a source of sweeping stripping voltage and a source of pulse voltage for impressing plating voltage, stripping voltage and pulse voltage rspectively across said working electrode and said counter electrode; a current-voltage converter for converting the current flowing through the working electrode into voltage for producing two sample voltages; voltage holding means for holding said two sample voltages; and a differential amplifier for amplifying the difference between said two sample voltages held by said voltage holding means, characterized in that said source of pulse voltage is constructed to generate a pulse voltage having a period of from 16.7 to 400 milliseconds.

DESCRIPTION OF THE PREFERRED EMBODIMENTS

The detail of the basic construction of the apparatus of this invention will now be described with reference to the block diagram shown in FIG. 7, in which reference numeral 1 designates an electrolytic cell containing a solution to be measured and a working electrode 2 and a counter electrode 3 immersed therein. Further, a reference electrode 4 is also disposed in the cell 1 for compensating for the effect caused by the variation in the concentration of a component to be analyzed in the liquid being measured. Reference electrode 4 is connected to an addition circuit 9 via an impedance converter 8.

A plating voltage source 6 and a sweeping stripping voltage source 7 are connected to the counter electrode 3 respectively through contacts $SW_4$ and $SW_5$ of a transfer switch 5 and the addition circuit 9. A source of pulse 10 constructed to produce a DC pulse having an amplitude of 10 to 100 millivolts, for example, is connected to the counter electrode 3 via contact $SW_3$ of a timing switch 11 and the addition circuit 9. The pulse having a duration or width of 8.3 to 100 milliseconds determined by the opening and closing of the contact $SW_3$ is impressed across the working electrode 2 and the counter electrode 3. The waveform of the pulse is preferably to be rectangular or similar shapes.

The working electrode 2 is connected to voltage holding means including two voltage holders 13 and 14 respectively through a current-voltage converter 12 and contacts $SW_1$ and $SW_2$ of the timing switch 11. The two sample voltages held by voltage holders 13 and 14 are applied to a differential amplifier 15 to produce an output signal.

The detail of respective elements described above will now be described.

Any type of the electrolytic cell 1 may be used provided that it is suitable to contain the liquid to be measured. For example, cylindrical or inverted cone shaped container made of glass, plastics, etc. may be used.

Among the working electrodes 2 that can be used in this invention are included a hanging mercury drop electrode (HMDE), an electrode made of platinum, nickel, tungsten, graphite or glassy carbon, an electrode prepared by moulding a mixture of a carbon powder and a hard polymer, epoxy resin for example, a carbon paste electrode prepared by moulding a mixture of a carbon powder and paraffin, a mercury film electrode comprising a solid electrode coated with a mercury film, etc.

Among these electrodes, the hanging mercury drop electrode (HMDE) is especially suitable for use as the working electrode of the apparatus of this invention. In principle, this electrode comprises a capillary tube having a mercury pool and a microhead connected to the capillary tube. Various types of HMDE are known in the art and any one of them can be used in this invention.

Although HMDE is suitable, when the temperature of the mercury varies during use, the surface area of the mercury drop varies thus degrading the reproducibility of the result of measurement. Further, presence of air bubbles in the mercury pool makes it difficult to adjust the size of the mercury drop. Accordingly, it is essential to maintain the room temperature at a constant value during the use of the HMDE. Moreover, it is necessary to take care not to entrain air bubbles in the mercury while pouring the same.

Figure 8:
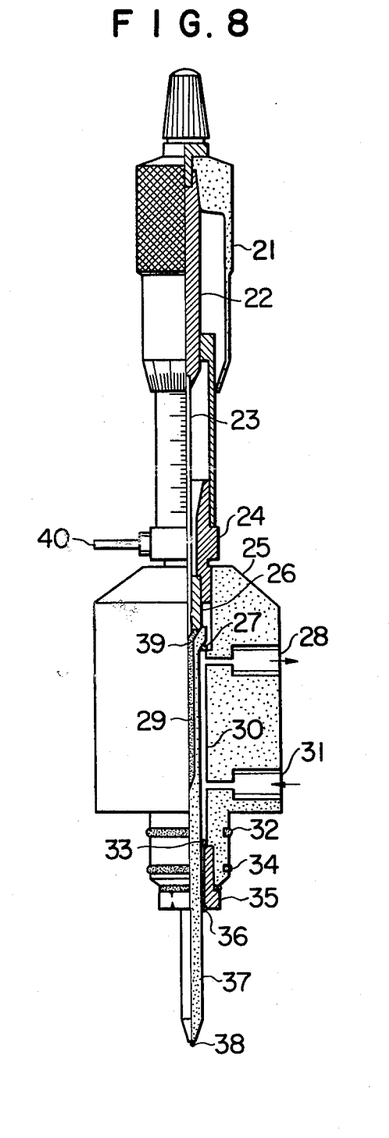
FIG. 8 is a side view, partly in longitudinal section, showing one example of the hanging mercury drop electrode utilized in this invention.

The following HDME from which defects described above have been eliminated is especially suitable for use in this invention wherein a capillary tube provided with a mercury pool is connected with a microhead through a joint in the body of the electrode and constant temperature cooling water is circulated about the mercury pool, as illustrated in FIG. 8. When a knob 21 of the microhead is rotated, a plunger 23 is reciprocated in the longitudinal direction through a feed screw rod 22. The microhead is connected to the main body 25 through a joint 24. The lower end of the joint 24 is connected to a mercury pool 29 via a packing 26. A space 30 for circulating cooling water surrounds the mercury pool 29. The cooling water maintained at a constant temperature is admitted into the space 30 through an inlet port 31 and discharged through an outlet port 28 as shown by arrows. A hollow capillary tube 37 extends downwardly from the mercury pool 29 and a mercury drop 38 is formed at the lower end of the capillary tube. An electrode terminal 40 is connected to the joint 24. The capillary tube 37 is provided with a flange 39 at its upper end and inserted into the central bore of the main body 25. O-rings 27 and 33 are interposed between the capillary tube 37 and the main body 25 for sealing the space 30. The O-ring 33 is maintained in position by a stationary screw bushing 35 at the lower end of the main body. An O-ring 36 is provided to seal the gap between the capillary tube 37 and the stationary screw bushing 35 whereas O-rings 32 and 34 are provided for mounting the electrode on the electrolytic cell. With this construction since the temperature of the mercury pool is maintained at a constant value it is not necessary to maintain the temperature of the measuring room at a constant value. Where the main body is made of transparent material such as acrylic resin it is possible to readily confirm the presence or absence of air bubbles in the capillary tube. Moreover, as the various parts of the electrodes are interconnected through the joint, packing and O-rings their assembling and disassembling are easy.

As has been described above, a solid electrode made of metal or carbon can also be used as the working electrode of this invention. Although a metal electrode is easier to handle than a mercury electrode, as the surface conditon of the electrode varies during use thereby deteriorating the reproducibility it is necessary to subject the electrode to a regeneration treatment requiring a substantial labour and time.

Figure 9:
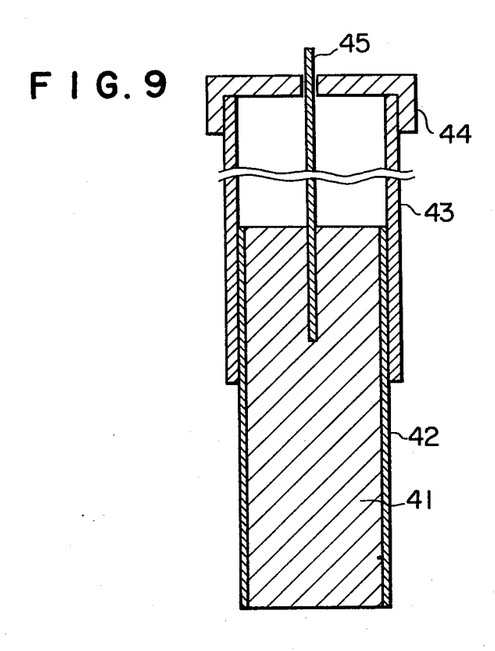
FIGS. 9 and 10 are longitudinal sectional views showing two examples of the solid electrode.
Figure 10:
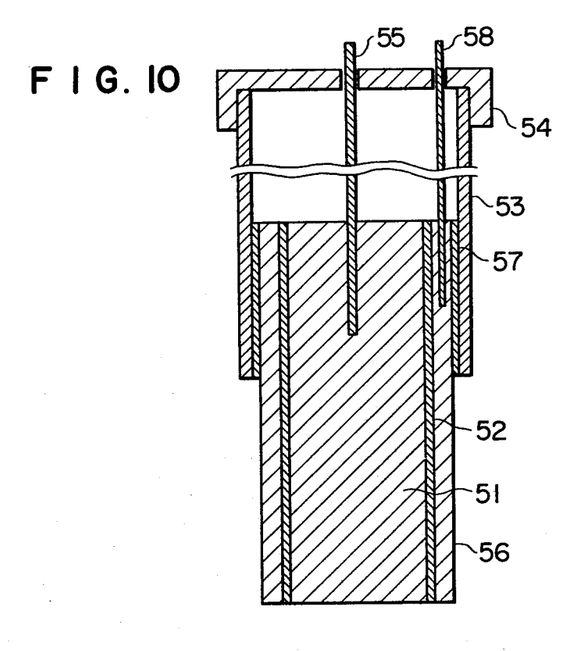

A solid electrode prepared by moulding a mixture of a powder of electroconductive substance and a soft polymer is free from these difficulties. As the powder of the electroconductive substance is preferred a powder of carbonaceous substance such as carbon black, graphite and glassy carbon but a powder of such metals as platinum, gold, silver, copper, etc. can also be used. Preferably, the particle is relatively fine, a preferred average particle diameter being less than about 10 microns, more preferably from about 0.05 to 5 microns. As the soft polymer may be used silicone rubbers, fluorinated rubber, polyethylenes, neoprenes, natural rubber, polysulfide rubber, nitrile rubber and so forth. Silicone rubbers are especially suitable. Preferred hardness of the soft polymer is about HS 30 to HS 90 measured by a spring according to JISK 6380, more preferably from about HS40 and HS80. Although the percentage of the electroconductive substance differs dependent upon the electroconductivity and particle size thereof, in the case of a carbon powder the percentage usually ranges from 30 to 80% by weight, preferably from 30 to 60%, whereas in the case of a metal powder from 10 to 80%, more preferably from 20 to 60%, by weight. The pointed surface of the electrode made of conductive substance can readily be regenerated by cutting it with a knife blade. FIGS. 9 and 10 are longitudinal sectional views showing examples of such solid electrode.

FIG. 9 shows an example of a solid electrode, comprising a rod shaped electrode 41 having a circular or square cross-section and made of an electroconductor and an insulating tube 42 covering the electrode. The insulating tube comprises a heat shrinkable tube made of Teflon, silicones or polyethylenes. It is advantageous that such insulating tube should be soft and can be cut readily for regenerating the electrode surface. The covered electrode rod 41 snugly fits in the opening at one end of a cylindrical or square electrode holder 43 made of glass, plastics or metal. To ensure snug fit the inner diameter of the electrode holder 43 is made to be slightly smaller than the outer diameter of the insulating tube or a binder may be used at the joint. If desired, the joint between the electrode holder 43 and the insulating tube may be covered by a heat shrinkable tube. A cap 44 is threaded, force-fit or bonded to the upper end of the electrode holder 43 and a lead conductor 45 extends through cap 44 to be received in an opening in the upper end of the electrode rod 41.

FIG. 10 shows an example of a composite electrode wherein an electrode rod 51 is contained in an electrode cylinder 56 via an insulating tube 52. The upper end of the electrode cylinder 56 is snugly held by the lower end of electrode holder 53 via an insulating tube 57. Lead conductors 55 and 58 extend through cap 54 to be received in the openings at the upper ends of the electrode rod 51 and the electrode cylinder 56, respectively. In the composite electrode of this type, the bottom surface of the electrode rod 51 is used as the working electrode whereas the outer periphery of the electrode cylinder 56 as the counter electrode having a large surface area.

Except the hanging mercury drop electrode, the working electrode 2 may be either a stationary type or a rotary type. The counter electrode 3 may be made of platinum, tungsten or carbon, for example, whereas as the reference electrode may be used a calomel electrode, a sliver-silver chloride electrode, etc.

The construction and operation of the source system including plating voltage source 6, sweeping stripping voltage source 7, pulse voltage source 10 and adder 9, and in some case further including reference electrode 4 and impedance converter 8; the switch system including plating-stripping transfer switch 5 and timing switch 11; the output system including current-voltage converter 12, voltage holders 13 and 14 and differential amplifier 15 are well known in the art so that their detailed description is believed unnecessary.

For example, each one of the plating voltage source 6 and the pulse voltage source 10 may comprise a battery and a potentiometer. The sweeping stripping voltage source 7 may comprise an integrating circuit constituted by an operational amplifier, capacitor and a resistor, and the impedance converter 8 may comprise a voltage follower circuit utilizing an operational amplifier, for example. As the addition circuit 9 may be used an adder including an operational amplifier. The plating-stripping transfer switch 5 may comprise a reed switch, for example.

The timing switch 11 may comprise a semiconductor analogue switch, while the current-voltage converter 12 may comprise a current-voltage conversion circuit including an operational amplifier, for example. The voltage holders 13 and 14 may be constituted by operational amplifiers. The differential amplifier 15 may comprise an operational amplifier, for example.

These circuits operate to produce an output according to the following equation

Output = $IS_2 - IS_1$.

If a correcton term is used for this mathematical operation, a circuit for operating the correction term is added to the differential amplifier 15.

Figure 7:
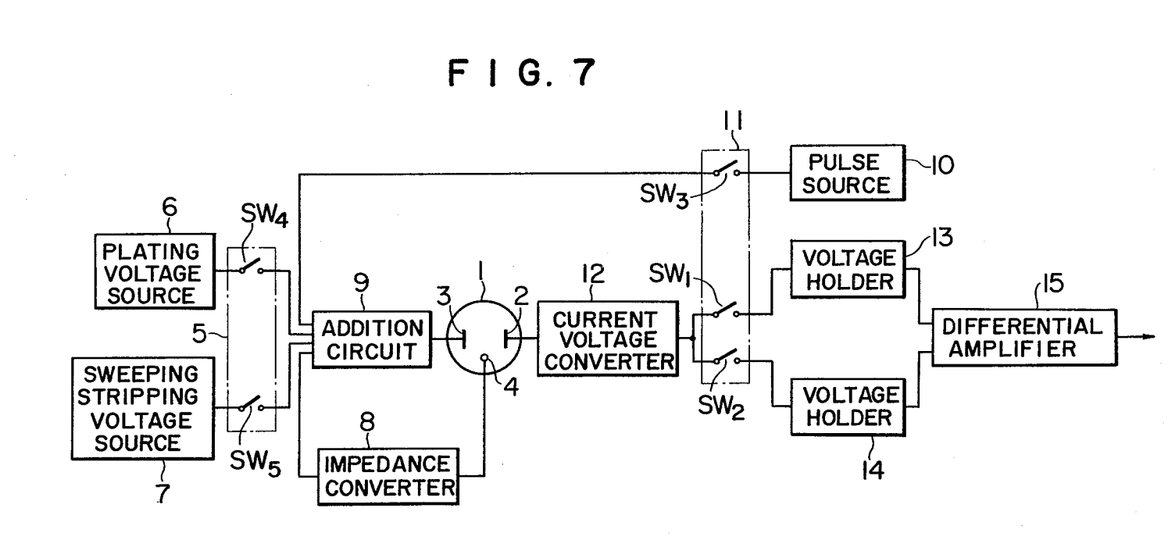
FIG. 7 is a block diagram showing one example of the construction of the apparatus of this invention.
Figure 11:
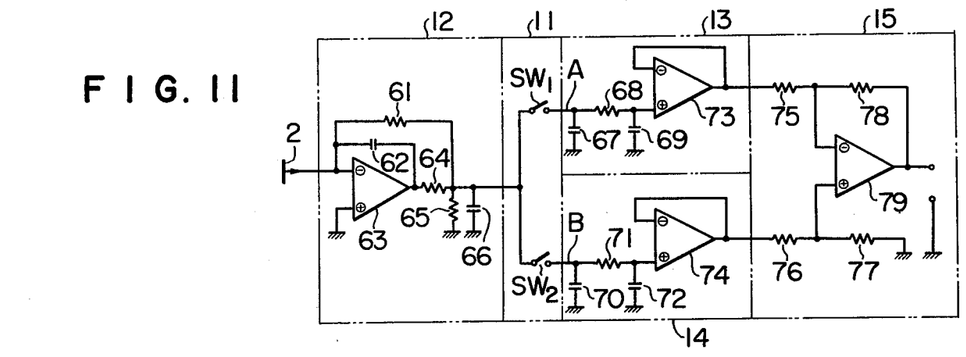
FIGS. 11 and 12 are connection diagrams showing two types of the output circuit utilized in this invention.

FIG. 11 shows one example of the output circuit system of the apparatus of this invention wherein 2, 11 through 15 designate corresponding elements shown in FIG. 7. More particularly, working electrode 2 is connected to the input terminal of the current-voltage converter 12 and the output terminal thereof is connected to the input terminal of the timing switch 11. The circuit including a capacitor 62 grounded through resistors 64 and 65 comprises a so-called roll off circuit and is used for eliminating noise. Capacitor 66 is provided for the same purpose.

The output from an operational amplifier 63 comprising a portion of the current-voltage converter 12 is applied to inputs A and B of voltage holders 13 and 14 respectively through switch contacts $SW_1$ and $SW_2$. A circuit comprising resistor 68 and capacitors 67 and 69 and connected between input terminal A and an operational amplifier 73 of the voltage holder 13 comprises a $\pi$ type filter and the voltage is held by capacitor 69. The output from the operational amplifier 73 is fed back to an input ⊖ for forming the so-called voltage follower. This output is also connected to one end of resistor 75 of the differential amplifier 15. In the same manner, the input terminal B of the voltage holder 14 is connected to one end of resistor 76 of the differential amplifier 15 via a π type filter including resistor 71 and capacitors 70 and 72, and an operational amplifier 74.

The other ends of resistors 75 and 76 of the differential amplifier 15 are connected to ⊖ and ⊕ input terminals, respectively, of the operational amplifier 79 whose output is fed back to the ⊖ input terminal via resistor 78. The ⊕ input terminal of the operational amplifier 79 is grounded via resistor 77 to form a differential amplifier circuit.

Figure 12:
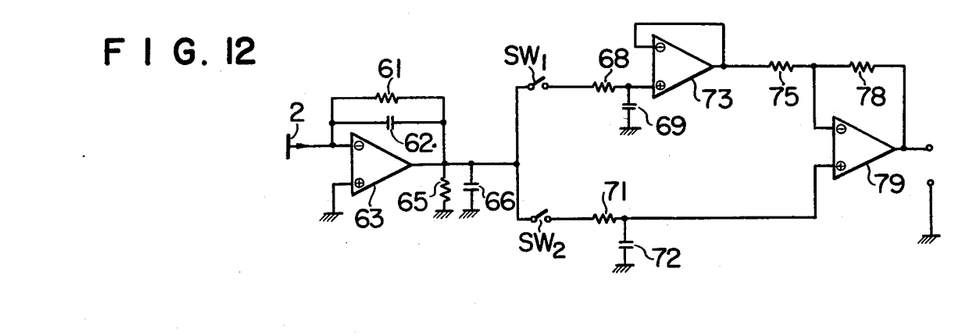

Among various elements of the output circuit system shown in FIG. 11, capacitors 67 and 70 are used to eliminate high frequency components. The circuit including operational amplifier 74 and resistors 76 and 77 is convenient to check the operation of the circuit but these circuit elements may be omitted, as shown in FIG. 12.

This invention is characterized in that pulse voltage source utilized in the apparatus for use in DPASV is constructed to apply a pulse voltage having especially short period of 16.7 to 400 milliseconds. As has been pointed out before the sensitivity is improved in inverse proportion to the pulse period. On the other hand, it is advantageous that the pulse period should be an integer multiple of the period of the source used in order to decrease noise. For this reason, the lower limit of the pulse period should be 16.7 milliseconds where a commercial source having a frequency of 60 Hz is used whereas 20 milliseconds for a source of 50 Hz. In view of the response speed of the analogue switch, it is not advantageous to decrease further the pulse period. More preferred pulse period ranges from 33.4 to 200 millisecond.

Figure 13:
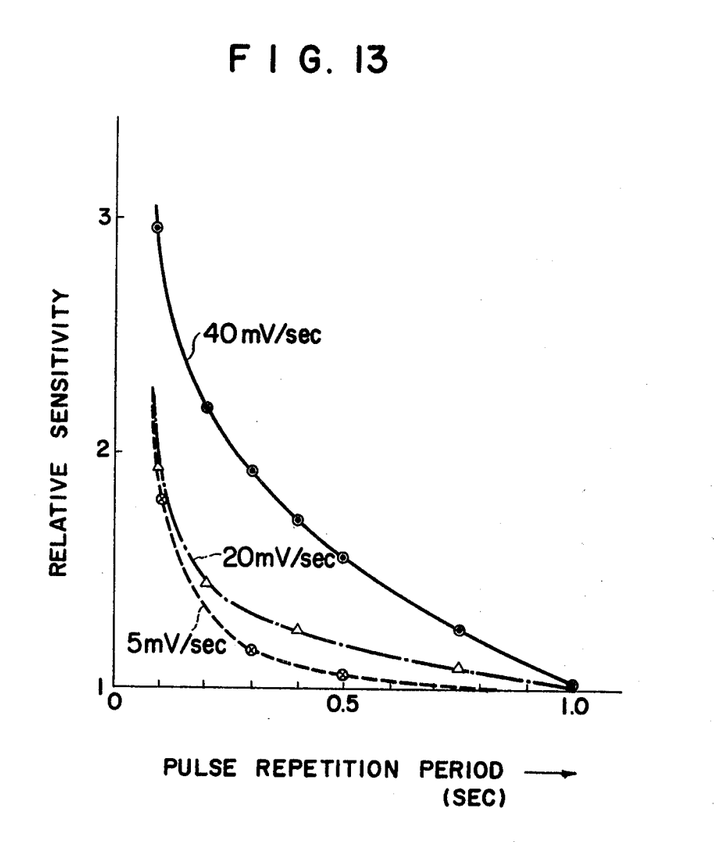
FIG. 13 is a graph showing the relationship between the pulse repetition period, and the relative sensitivity by utilizing the sweeping speed as a parameter.

As described above, the sensitivity can be improved by decreasing the pulse period. The decrease in the pulse period has an additional advantage of increasing the speed of analysis. More particularly, in DPASV, one measurement is done at each pulse period and the analysis is based on the accumulation of respective measurements. Accordingly, shortening of the pulse period results in the increase of the measuring points in a unit time so that it is possible to increase the sweeping speed in proportion thereto. The sweeping speed utilized in this invention is usually from 1 to 90 mv/sec, preferably from 20 to 60 mv/sec. As shown in FIG. 13, as the sweeping speed is increased the sensitivity is increased owing to the decrease in the pulse period. By modifying the apparatus of this invention in the following manner, its characteristics can be improved further.

Where measurements are made sequentially by using the apparatus of this invention, after completion of one measurement the voltage held by the voltage holders affects the accuracy of the next analysis. This problem can be solved by discharging the voltage held by the voltage holders each time when a measurement has completed, for example, by grounding the input terminals of the voltage holders through switches.

Figure 14:
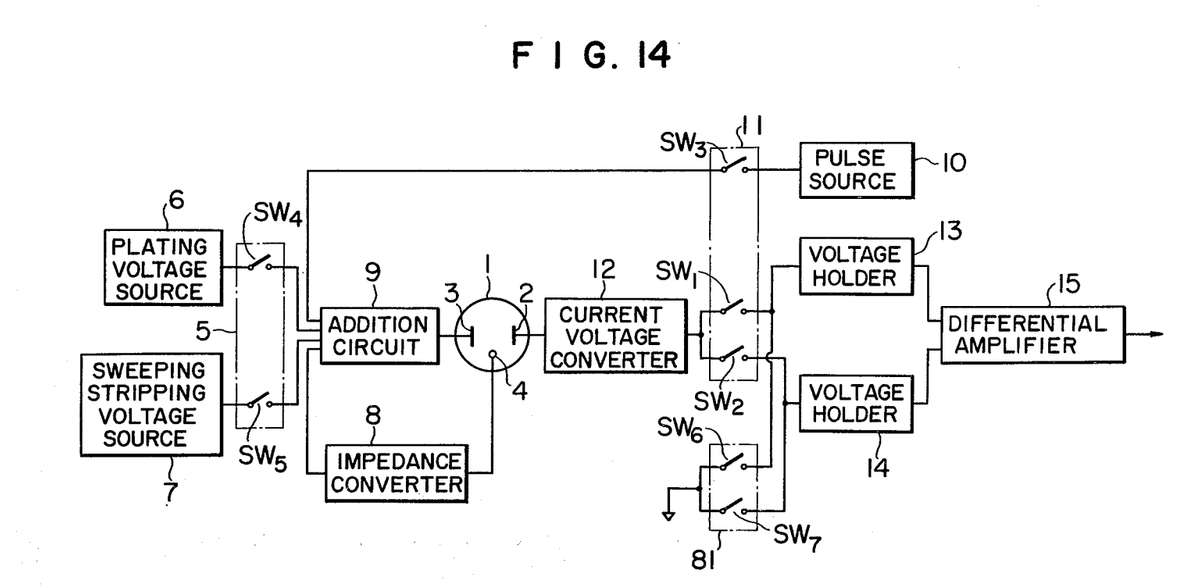
FIG. 14 is a block diagram showing a modified embodiment of this invention wherein the input terminals of voltage holders are grounded through switches.
Figure 15:
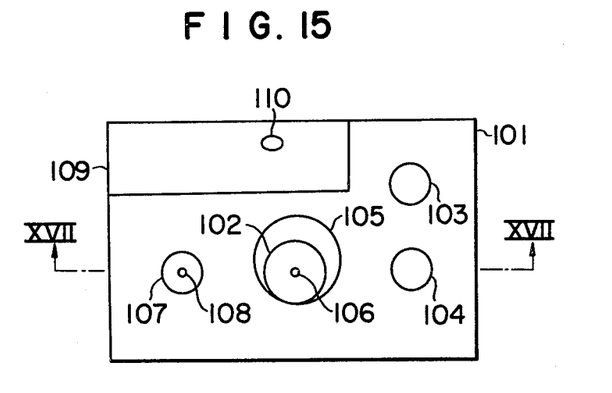
FIG. 15 is a plan view of a measuring cell utilized in this invention.
Figure 16:
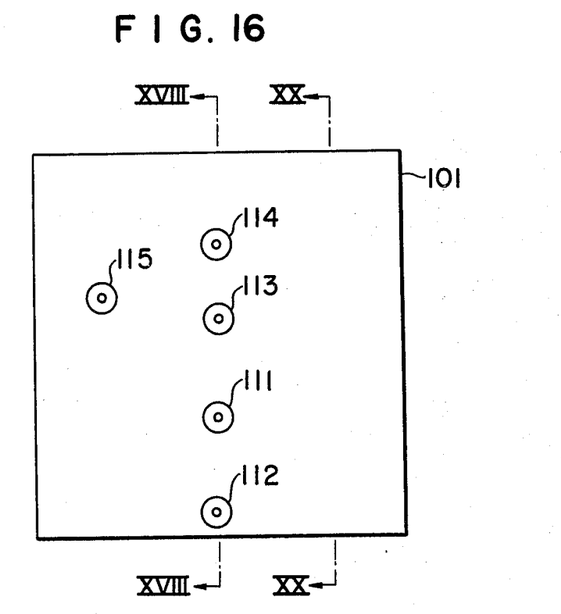
FIG. 16 is a rear view of the measuring cell shown in FIG. 15.

FIG. 14 is a block diagram showing one example of such modification wherein numerals 1 through 15 represent the same elements as those shown in FIG. 7. As shown, the input terminals of the voltage holders 13 and 14 are grounded through contacts $SW_6$ and $SW_7$ of timing switch 81 which may be a semiconductor switch (analogue switch) as before. During measurement contacts $SW_6$ and $SW_7$ are opened but closed upon completion of the measurement for discharging the voltage held by the voltage holders. Although closing and opening of these contacts may be made manually, it is advantageous to operate them by means of an automatic sequence circuit which as is well known in the art is usually constituted by relays, timers and logic elements, integrated circuits, for example.

To analyze according to DPASV, usually inert gas, such as nitrogen or hydrogen is firstly blown into the solution being analyzed and contained in the electrolytic cell for removing oxygen dissolved in the solution (oxygen removing step). Thereafter, the plating voltage is impressed upon the working electrode for plating or depositing the component to be analyzed (plating step). Then, the sweeping stripping voltage and pulse voltage are applied to strip the component to be analyzed. (stripping step). During the oxygen removing step and the plating step described above, for the purpose of improving the efficiency, the solution in the electrolytic cell is usually stirred.

One many expect that the efficiency can be improved by increasing the stirring speed. Actually, however, it is advantageous to stir at a relatively low speed during the oxygen removing step and at a relatively high speed during the plating step. Where a high speed stirring is effected during the oxygen removing step there is a tendency to entrain air bubbles in the solution. When a HMDE is used there is a fear that air bubbles may deposit on the mercury drop or the mercury drop may fall down. For this reason, the preferred number of revolutions of the stirrer during the oxygen removing step is generally from 300 to 800 RPM, more preferably from 300 to 500 RPM although it depends upon the shape and size of the stirrer and the size of the electrolytic cell.

During the plating step, the tendency of entraining air bubbles is small and the detection sensitivity increases with the stirring speed. Accordingly, a preferred number of revolutions of the stirrer during the plating step is higher than 1,000 RPM, more preferally high than 1,500 RPM. Although high stirrer speed is preferred, the upper limit of conventional stirrers is about 2,000 RPM. Where a HMDE is used there is a possibility that the mercury drop may be caused to fall down by the vortex created by high speed stirring, so that it is advantageous to provide a buffle plate in the electrolytic cell to prevent generation of the vortex.

Of course, the switching between the numbers of revolutions of the stirrer during the oxygen removing step and during the plating step can be done manually, but it can also be done automatically by utilizing a sequence circuit combined with a time setting circuit as is well known in the art.

As described above, a reference electrode is usually disposed in the electrolytic cell of the apparatus of this invention. In such case, a so-called H type electrolytic cell is used wherein a working electrode cell containing a working electrode and a counter electrode, and a reference electrode cell containing a reference electrode are interconnected through a salt bridge. Usually such H type cell is made of glass and can be advantageously used in this invention.

However, in the H type cell made of glass it is difficult to make short the length of the salt bridge, e.g. less than several centimeters. As a result, the salt bridge causes a voltage drop causing increase in the non-faradic current as well as decrease in the measuring accuracy. Further, ions, for example chlorine ions, in the reference electrode cell migrate into the working electrode cell through the salt bridge thereby interferring with the measurement. These deflects can be obviated by using a measuring cell having the following construction.

More particularly, such measuring cell comprises an electrolyte solution cell disposed between the working electrode cell and the reference electrode cell, and wherein these cells are integrally formed in a block.

FIGs. 15 through 20 show one example of the measuring cell having a construction just described, wherein 101 shows the main body of the cell, 102 a working electrode cell, 103 a reference electrode cell, 104 an electrolyte solution cell, and 117 and 123 liquid communicating passages.

More particularly, the main body 101 is a block made of plastics, glass, metal or the like. From the standpoint of inspection of the interior and easiness of working it is advantageous to fabricate it with a transparent plastic, for example acrylic resin.

The working electrode cell 102 takes the form of a cylindrical bore vertically extending through the main body 101 and provided at the bottom with a sample inlet port 112 and a discharge port 106 for the liquid to be measured. Along the cylindrical bore are provided an opening 111 for inserting the counter electrode, an inert gas inlet port 113, a standard sample pouring port 110 and a sample overflow port 114.

The working electrode 120 is inserted into the working electrode cell 102 through the opening at the upper end 105 thereof. Preferably the axis of the end portion 105 is slightly eccentric with respect to the axis of the working electrode cell. During the measuring operation the liquid being measured 121 contained in the working electrode cell 102 is stirred by a rotor 122 located at the bottom of the cell. Air bubbles formed by the entrained air have a tendency to gather at the center of the cell. Consequently, if the working electrode 120 were positioned at the axial center of the working electrode cell 102 air bubbles would deposit on the electrode surface, thus decreasing the measuring sensitivity. However, when the working electrode is positioned slightly eccentrically as above described, deposition of the air bubbles can be prevented efficiently. Moreover, as the linear velocity of the liquid becomes higher at the peripheral portion than at the central portion, the measuring accuracy is improved. When a lens shaped projection 119 is provided on the outer surface of the main body 101 at a position corresponding to that of the working electrode 120 it is advantageous to observe the condition of the working electrode.

Figure 17:
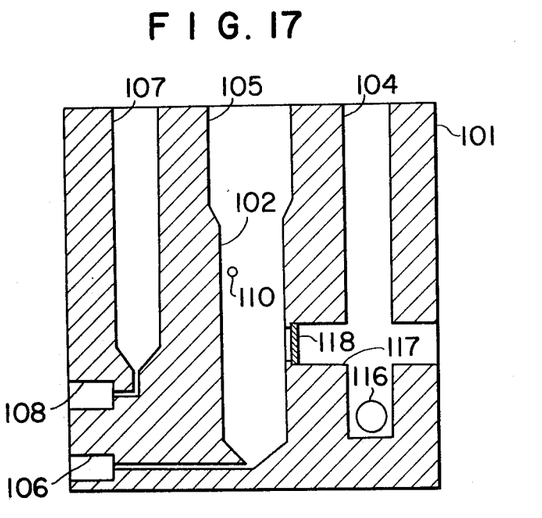
FIG. 17 is a cross-sectional view of the cell shown in FIG. 15 taken along a line XVII—XVII.
Figure 18:
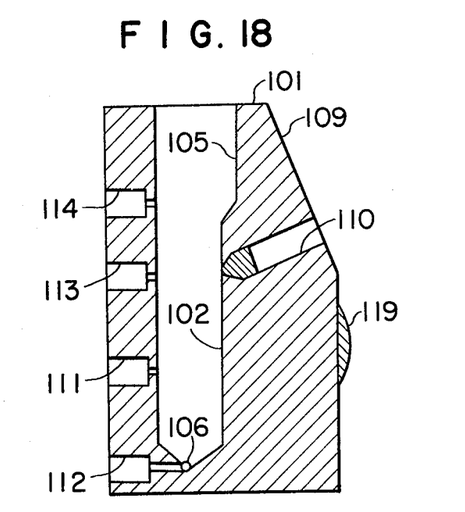
FIG. 18 is a sectional view taken along a line XVIII—XVIII in FIG. 16.
Figure 19:
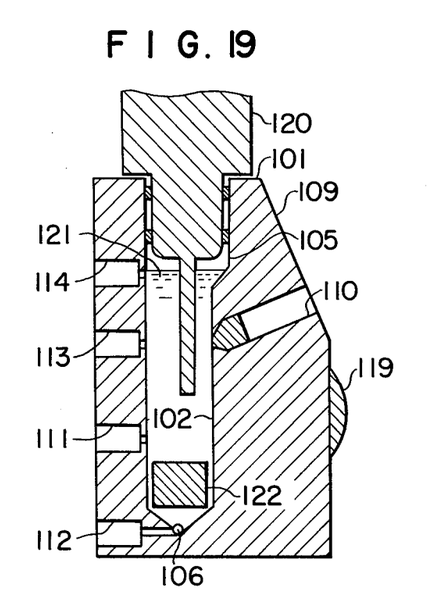
FIG. 19 is a sectional view of the cell shown in FIG. 18 with a working electrode mounted thereon and FIG. 20 is a sectional view of the cell shown in FIG. 16 taken along a line XX—XX.
Figure 20:
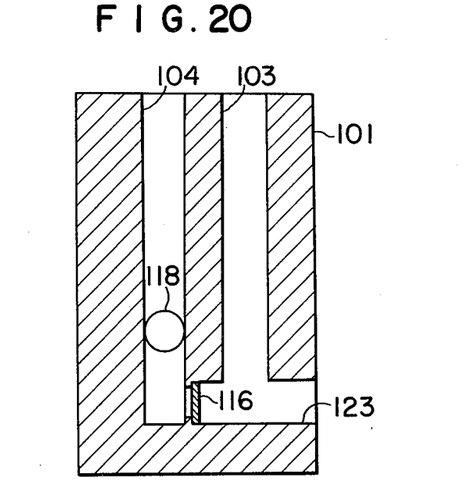

The reference electrode cell 103 and the electrolyte solution cell 104 take the form of cylindrical bores parallel with the working electrode cell 102. The bottoms of the cells 103 and 104 are intercommunicated through a liquid communicating passage 123, whereas the electrolyte solution cell 104 is communicated with the working electrode cell 102 through a communication passage 117 as shown in FIG. 17.

An electrode liquid is filled in the reference electrode cell 103 and the reference electrode is hung through its upper opening.

The liquid communication passages 117 and 123 are formed to open to the outer surface of the main body 101 and provided with partition walls 118 and 116 respectively made of ceramic, porous fluorinated polymer or agaragar for separating intercommunicated cells. The joint between the communication passage 123 and the electrolyte solution cell 104 is located at a lower level than the joint between the passage 117 and the electrolyte solution cell 104. Preferably, the length of the liquid communication passages 117 and 123 is made to be short, for example 5 to 30 mm, preferably 5 to 20 mm. The outer openings of these passages are closed by plugs, not shown.

Although it is preferred to charge in the electrolyte solution cell 104 the same electrolyte as the supporting electrolyte for the solution being measured, usually, however, an aqueous solution of potassium chloride or potassium nitrate, is used.

Admission of the solution being measured into the working electrode cell 102 is made by continuously admitting the solution through inlet port 112, causing it to overflow, and then stopping the admission when the inside of the cell is throughly washed and replaced by the solution.

After completion of the measurement, the solution is discharged into a waste tank 107 through discharge opening 106, and a conduit (not shown) between the same and an opening 115 leading to the tank 107 by operating a suction pump (not shown) mounted in the upper opening of the waste tank 107 which is in parallel with the working electrode cell 102. Then the waste solution is discharged to the outside through the upper opening of the waste cell 107.

Where a mercury electrode is used as the working electrode, mercury is separated in the waste tank 107 and discharged through discharge port 108.

In the measuring cell described above, since the length of the salt bridge is small, not only the non-faradaic current is small but also as the movement of the content between intercommunicated cells does not interfere with the measurement, the cell is especially suitable for measuring a small quantity of ions. Moreover, as the entire cell is manufactured by working a single block, it has a large mechanical strength and is easy to handle.

We claim:

1. A method of differential pulse anodic stripping voltammetry comprising the steps of
    filling a solution containing ions of a metal to be analyzed into an electrolytic cell having a working electrode and a counter electrode,
    applying a plating voltage across the counter electrode and the working electrode to plate the same with the metal,
    applying across the counter electrode and the working electrode a DC stripping voltage having superimposed thereon a pulse voltage having a repetition period of 16.7 to 400 milliseconds in order to strip the metal that has been plated on the working electrode by the plating voltage,
    measuring a first sampling current which flows through the working electrode during a predetermined interval in which the pulse voltage is not applied,
    measuring a second sampling current which flows through the working electrode while the pulse voltage is applied, and
    determining the difference between the first and second sampling currents.

2. The method according to claim 1 wherein the repetition period of the pulse voltage is 33.4 to 200 milliseconds.

3. The method according to claim 1 wherein the duration of the pulse voltage is 8.3 to 100 milliseconds.

4. The method according to claim 1 wherein the stripping voltage is swept at a speed of 10 to 90 millivolts/sec.

5. The method according to claim 4 wherein the sweeping speed ranges from 20 to 60 millivolts/sec.

6. The method according to claim 1 wherein the first sampling current is measured in an interval immediately prior to each pulse voltage.

7. The method according to claim 1 wherein the second sampling current is measured during a predetermined interval of the latter half of each pulse voltage.

8. Differential pulse anodic stripping voltametry comprising:
   an electrolytic cell having a working electrode and a counter electrode;
   a source of plating voltage, a source of sweeping voltage and a source of pulse voltage having a repetition period of 16.7 to 400 milliseconds for impressing plating voltage, stripping voltage and pulse voltage respectively across the working electrode and the counter electrode;
   a current-voltage converter for converting the current flowing through the working electrode into voltage for producing two sample voltages;
   voltage holding means for holding the two sample voltages; and
   a differential amplifier for amplifying the difference between the two sample voltages held by the voltage holding means.

9. The apparatus according to claim 8 wherein the period of the pulse voltage is 33.4 to 200 milliseconds.

10. The apparatus according to claim 8 wherein the duration of the pulse voltage is 8.3 to 100 milliseconds.

11. The apparatus according to claim 8 wherein the stripping voltage has a sweeping speed of 1 to 90 millivolts/sec.

12. The apparatus according to claim 11 wherein the sweeping speed is 20 to 60 millivolts/sec.

* * * * *